US010420660B2

(12) United States Patent
Shobayashi

(10) Patent No.: US 10,420,660 B2
(45) Date of Patent: Sep. 24, 2019

(54) FLEXIBLE STENT

(71) Applicant: WORLD MEDISH TECHNOLOGY CO., LTD., Tokyo (JP)

(72) Inventor: Yasuhiro Shobayashi, Tokyo (JP)

(73) Assignee: WORLD MEDISH TECHNOLOGY CO., LTD., Tokyo (JP)

( * ) Notice: Subject to any disclaimer, the term of this patent is extended or adjusted under 35 U.S.C. 154(b) by 94 days.

(21) Appl. No.: 15/128,796

(22) PCT Filed: Mar. 26, 2014

(86) PCT No.: PCT/JP2014/058415
§ 371 (c)(1),
(2) Date: Dec. 21, 2016

(87) PCT Pub. No.: WO2015/145596
PCT Pub. Date: Oct. 1, 2015

(65) Prior Publication Data
US 2017/0100268 A1  Apr. 13, 2017

(30) Foreign Application Priority Data
Mar. 25, 2014 (JP) ................. 2014-061130

(51) Int. Cl.
*A61F 2/915* (2013.01)

(52) U.S. Cl.
CPC .... *A61F 2/915* (2013.01); *A61F 2002/91566* (2013.01); *A61F 2002/91583* (2013.01);
(Continued)

(58) Field of Classification Search
CPC .... A61F 2/915; A61F 2/07; A61F 2/82; A61F 2002/821; A61F 2002/825;
(Continued)

(56) References Cited

U.S. PATENT DOCUMENTS 5,776,161 A * 7/1998 Globerman ............... A61F 2/90
606/192
6,287,336 B1 * 9/2001 Globerman ............... A61F 2/90
623/1.15
(Continued)

FOREIGN PATENT DOCUMENTS

CN 1479596 A 3/2004
CN 1491097 A 4/2004
(Continued)

*Primary Examiner* — Alvin J Stewart
(74) *Attorney, Agent, or Firm* — Muncy, Geissler, Olds & Lowe, P.C.

(57) ABSTRACT

Provided is a flexible stent in which a free end strut does not tend to project outside when the stent is bent and shortening can be suppressed at the time of expansion of the stent. The flexible stent includes annular bodies having a wavy line pattern and connection elements that connect the annular bodies. The wavy line pattern is formed by V-shaped elements, in which two leg parts are joined by an apex part, being connected in a state where the apex parts alternately face opposite directions in an axial direction. A bending direction of one end part of the connection element and a bending direction of another end part thereof are opposite to one another. The end part of the connection element is connected to a portion other than the apex part of the V-shaped element of the adjacent annular body with the end part of the connection element being extended in a direction different from the direction in which the leg part extends. When viewed in a radial direction (RD), the direction in which an intermediate part of the connection element extends is oblique to the axial direction (LD). One of the two leg parts extends along the intermediate part of the connection element.

11 Claims, 13 Drawing Sheets

(52) U.S. Cl.
CPC ............... *A61F 2230/0023* (2013.01); *A61F 2230/0054* (2013.01)

(58) Field of Classification Search
CPC ........ A61F 2002/828; A61F 2/88; A61F 2/89; A61F 2002/91533; A61F 2002/91541; A61F 2002/91525; A61F 2002/9155; A61F 2002/91583
USPC ........................................................ 623/1.16
See application file for complete search history.

(56) References Cited

U.S. PATENT DOCUMENTS

| | | | |
|---|---|---|---|
| 6,325,821 B1* | 12/2001 | Gaschino | A61F 2/91 606/194 |
| 6,331,189 B1* | 12/2001 | Wolinsky | A61F 2/91 623/1.15 |
| 6,334,870 B1* | 1/2002 | Ehr | A61F 2/91 623/1.1 |
| 6,334,871 B1* | 1/2002 | Dor | A61F 2/91 623/1.34 |
| 6,428,570 B1 | 8/2002 | Globerman | |
| 6,485,508 B1* | 11/2002 | McGuinness | A61F 2/91 623/1.15 |
| 6,613,080 B1* | 9/2003 | Lootz | A61F 2/91 623/1.15 |
| 6,949,120 B2* | 9/2005 | Kveen | A61F 2/91 623/1.15 |
| 6,955,686 B2* | 10/2005 | Majercak | A61F 2/91 623/1.15 |
| 7,004,968 B2* | 2/2006 | Lootz | A61F 2/91 623/1.15 |
| 7,766,956 B2* | 8/2010 | Jang | A61F 2/91 606/195 |
| 8,668,731 B2* | 3/2014 | Kveen | A61F 2/91 623/1.15 |
| 8,961,590 B2* | 2/2015 | Baillargeon | A61F 2/915 623/1.42 |
| 9,144,508 B2* | 9/2015 | Hebert | A61F 2/91 |
| 9,445,926 B2* | 9/2016 | Jang | A61F 2/91 |
| 2001/0044649 A1* | 11/2001 | Vallana | A61F 2/91 623/1.15 |
| 2002/0042648 A1* | 4/2002 | Schaldach | A61F 2/91 623/1.15 |
| 2002/0045934 A1* | 4/2002 | Jang | A61F 2/91 623/1.15 |
| 2002/0045935 A1* | 4/2002 | Jang | A61F 2/91 623/1.16 |
| 2002/0058990 A1* | 5/2002 | Jang | A61F 2/91 623/1.15 |
| 2003/0149469 A1* | 8/2003 | Wolinsky | A61F 2/91 623/1.11 |
| 2004/0106985 A1 | 6/2004 | Jang | |
| 2004/0133271 A1* | 7/2004 | Jang | A61F 2/91 623/1.42 |
| 2004/0172123 A1* | 9/2004 | Lootz | A61F 2/91 623/1.15 |
| 2005/0080479 A1* | 4/2005 | Feng | A61F 2/91 623/1.15 |
| 2008/0097587 A1* | 4/2008 | Moriuchi | A61F 2/91 623/1.35 |
| 2008/0228261 A1 | 9/2008 | Anukhin et al. | |
| 2008/0319528 A1* | 12/2008 | Yribarren | A61F 2/91 623/1.15 |
| 2009/0024205 A1* | 1/2009 | Hebert | A61F 2/91 623/1.16 |
| 2010/0286760 A1* | 11/2010 | Beach | A61F 2/88 623/1.22 |
| 2010/0331961 A1* | 12/2010 | Goetzen | A61F 2/915 623/1.16 |
| 2011/0238158 A1 | 9/2011 | Heringes et al. | |
| 2012/0029620 A1* | 2/2012 | Schroeder | A61F 2/915 623/1.16 |
| 2012/0029623 A1* | 2/2012 | Baillargeon | A61F 2/91 623/1.16 |
| 2012/0265292 A1 | 10/2012 | Kveen et al. | |
| 2013/0178928 A1* | 7/2013 | Vyas | A61F 2/915 623/1.16 |
| 2013/0317595 A1* | 11/2013 | Obradovic | A61F 2/07 623/1.13 |
| 2014/0081371 A1* | 3/2014 | Poehlmann | A61F 2/915 623/1.11 |
| 2018/0014953 A1* | 1/2018 | Yang | A61F 2/915 |

FOREIGN PATENT DOCUMENTS

| | | |
|---|---|---|
| JP | 2001-501488 A | 2/2001 |
| JP | 2003-250906 A | 9/2003 |
| JP | 2004-508880 A | 3/2004 |
| JP | 2004-202238 A | 7/2004 |
| JP | 2009-513300 A | 4/2009 |
| JP | 2010-233933 A | 10/2010 |
| WO | WO02/24109 A2 | 3/2002 |
| WO | WO02/24112 A2 | 3/2002 |
| WO | WO2007/053224 A1 | 5/2007 |

* cited by examiner

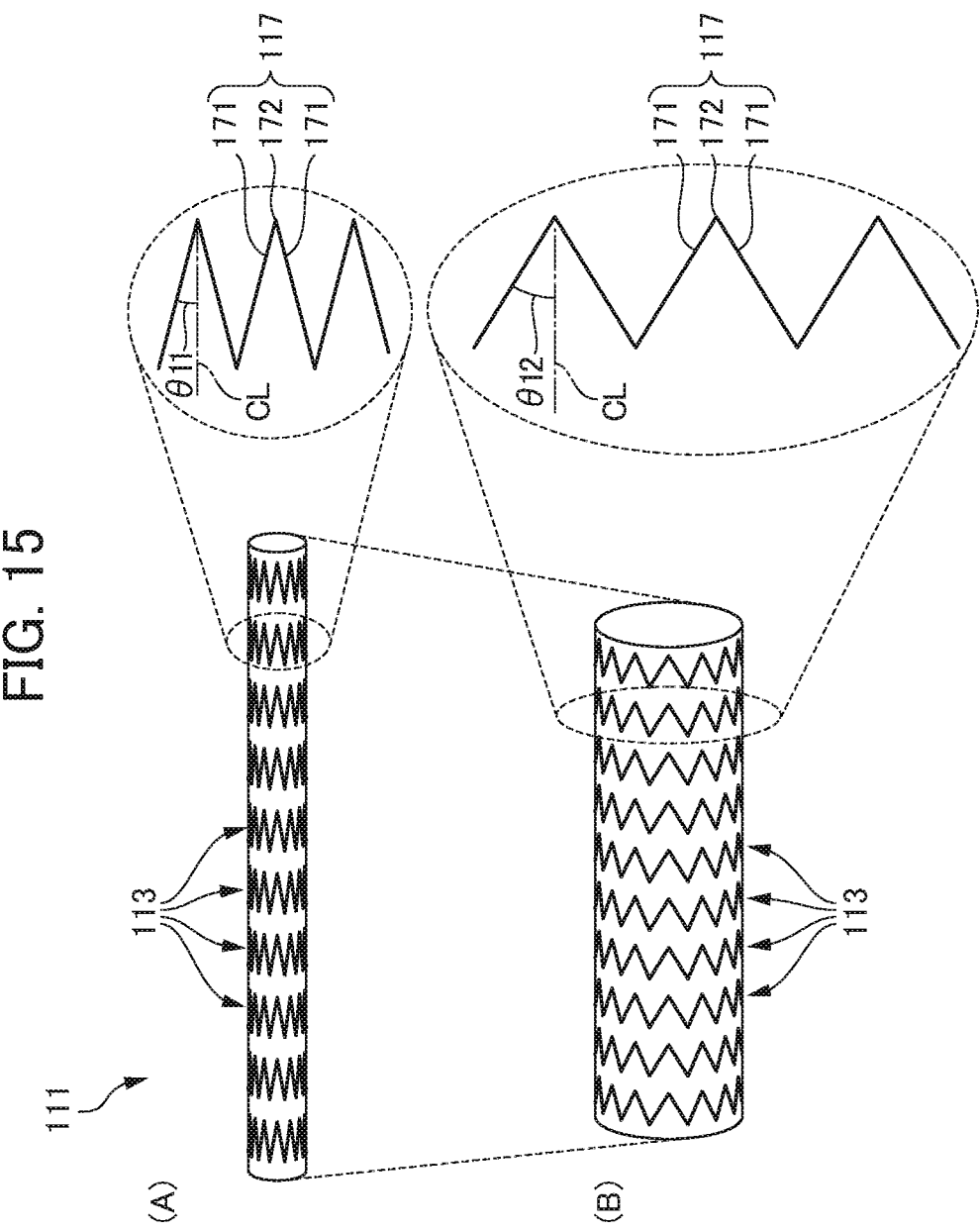

FLEXIBLE STENT

TECHNICAL FIELD

The present invention relates to a flexible stent placed in a luminal structure of a living body in order to expand lumen.

BACKGROUND ART

In a biological organ having a luminal structure such as blood vessels, the trachea and the intestines, when stenosis occurs therein, a cylinder-shaped flexible stent with mesh pattern is used in order to secure patency at a site of pathology by expanding an inner cavity at a narrowed part. These biological organs often have bent or tapered structures locally (i.e. a tubular structure of which sectional diameters of the inner cavity differ locally in an axial direction). Therefore, a stent having higher conformability has been desired which can flexibly adapt to such a complex vessel structure. Furthermore, in recent years, stents have come to also be employed for the treatment of cerebral blood vessels. Among tubular organs in a living body, the cerebral vessel system has a more complex structure. The cerebral vessel system has many bent sites and sites having tapered structures. Therefore, stents with particularly higher conformability have been required therein.

The structures of a stent generally include open cell structures and closed cell structures. In a stent having an open cell structure, an unconnected cell forms a strut having a free end. In a stent having a closed cell structure, every cell is connected and thus there is no strut having a free end.

Generally speaking, a stent having an open cell structure has a high conformability as compared to a stent having a closed cell structure, and thus the stent is suitable for placing in a tortuous tubular organ. Therefore, the stent is recognized as one having a stent structure which exerts remarkable mechanical flexibility in the axial direction. However, as illustrated in FIG. 13, in the stent 111 having an open cell structure, when bending and placing the stent 111 at a bent portion, a portion of the strut 117 easily protrudes radially outward from the stent 111 in a flared shape (refer to the portion surrounded by the dashed line of FIG. 13), a result of which there is a risk of damaging the tissue of a tubular organ in a body such as blood vessels. Furthermore, in particular, in bent blood vessels, when the strut 117 of the stent 111 located inside the blood vessel enters into a space located radially inside the stent 111, there is a risk of inhibiting blood flow and causing thrombus (refer to a portion surrounded by a short-long-dashed line of FIG. 13).

Furthermore, since the strut 117 protrudes in the stent 111 having the open cell structure, adhesion to the blood vessel wall BV (illustrated by a short-short-long-dashed line in FIGS. 13 and 14) is deteriorated in the bent blood vessel. Due to this, a space is generated between the stent and the blood vessel wall BV and thus there is a risk of causing thrombus herein. Moreover, since the adhesion to the blood vessel wall BV is deteriorated, stress concentration to the blood vessel wall BV results as illustrated in FIG. 14. Due to the stress concentration to the blood vessel wall BV by the stent 111, there is a risk of damaging the blood vessel wall BV since load is applied locally on the blood vessel wall BV. Moreover, at the portion to which stress concentration is applied, the risk of forming an inner membrane in excess in a blood vessel deformed by the stent 111 occurs, and thus lowers shear stress of the wall face which promotes regeneration of the membrane.

It should be noted that the two kinds of mechanical flexibilities in an axial direction (an axial direction, a central axial direction) and a radial direction (a vertical direction with respect to the axial direction) of the stent are said to be important for the purpose of realizing a stent with higher conformability. Herein, the flexibility in the axial direction refers to stiffness with respect to bending along the axial direction or the ease of bending, and thus is a property that is necessary for a stent to be flexibly bent along the axial direction so as to allow the stent to conform to a bent site of a tubular organ in a body. On the other hand, the flexibility in the radial direction refers to stiffness with respect to expansion and contraction in a vertical direction with respect to the axial direction or the ease of expansion and contraction, and thus is a property that is necessary for making the radius of a stent flexibly differ following the shape of an outer wall of a luminal structure of a tubular organ in a body so that the stent is in tight contact with the outer wall of the luminal structure.

In addition, regarding a stent, it is also an object to suppress shortening (refer to Japanese Unexamined Patent Application, Publication No. 2010-233933). When a stent mounted to a catheter in a state of being radially reduced is deployed (expanded) within a blood vessel during operation, the total length of the stent is shortened in the axial direction more than when crimped (radially reduced). The matter of the stent becoming shorter in the axial direction when expanding the stent, which is radially reduced, in such a way is referred to as "shortening". The cause of shortening is as follows. As illustrated in FIG. 15, when expanding the stent which is radially reduced, the angle of the apex 172 made by the leg portions 171 in the cell 117 which is directed in the axial direction LD becomes greater ($θ11<θ12$). It should be noted that the reference line CL is a line running parallel with the axial direction LD and passes through the apex 172.

Along with this, since a circular body 113 having the cell 117 expands in a circumferential direction, the whole stent 111 is shortened in the axial direction LD. In particular, for a stent having an open cell structure, since it is difficult to store the stent again in the catheter, the stent is required to be placed precisely in a single operation. However, such shortening increases the degree of difficulty of the stent treatment for a medical doctor.

Patent Document 1: Japanese Unexamined Patent Application, Publication No. 2010-233933

DISCLOSURE OF THE INVENTION

Problems to be Solved by the Invention

Therefore, it is an object of the present invention to provide a flexible stent in which, when bending and placing the stent, a strut having a free end does not easily protrude outward and in which, when expanding the stent, shortening of the stent is suppressed.

Means for Solving the Problems

The present invention relates to a flexible stent comprising: a plurality of circular bodies having a wavy-line pattern and arranged side-by-side in an axial direction; and a plurality of connection elements that connect the circular bodies that are adjacent and extend around an axis, wherein the wavy-line pattern is formed in such a manner that a plurality of V-shaped elements in a substantially V-shape made by coupling two leg portions at an apex are connected in a state in which each apex is arranged to alternately face an opposite direction in an axial direction, wherein a direction in which one end of the connection element is bent and a direction in which the other end of the connection element is bent are opposite, wherein the end of the connection element is connected with a portion other than the apex of the V-shaped element at the adjacent circular bodies by extending in a direction different from a direction in which the leg portion extends, wherein, when viewing in a radial direction perpendicular to the axial direction, a direction in which the intermediate portion of the connection element extends is inclined with respect to the axial direction, and wherein one of the two leg portions extends along the intermediate portion of the connection element.

The present invention may also be configured such that the end of the connection element is connected to the leg portion at each of the V-shaped elements of which the apex faces in the same direction in an axial direction.

The present invention may also be configured such that both of the two leg portions of the V-shaped element are arranged on the same side with respect to a reference line which runs in parallel with an axial direction and passes through the apex.

The present invention may also be configured such that the V-shaped element is rounded in a thickness direction of the V-shaped element along a shape of a virtual outer circumferential curved face of the flexible stent.

The present invention may also be configured such that a direction in which the end of the connection element extends and a direction in which the intermediate portion of the connection element extends are substantially perpendicular to each other.

The present invention may also be configured such that the intermediate portion of the connection element and the leg portion of the V-shape element are linear, and the leg portion that extends along the intermediate portion of the connection element runs in parallel with the intermediate portion of the connection element.

The present invention may also be configured such that the end of the connection element is connected in the proximity of a connection portion of the adjacent V-shaped elements in a circular direction of the circular body.

The present invention may also be configured such that the two leg portions of the V-shaped element consist of a long leg portion and a short leg portion, and the adjacent V-shaped elements in the circular direction of the circular body are connected so that the long leg portion is adjacent to the short leg portion.

The present invention may also be configured such that the end of the connection element is connected to the long leg portion of the V-shaped element.

The present invention may also be configured such that the end of the connection element is connected to a portion which is opposite to the apex at the long leg portion of the V-shape element and which is longer than the short leg portion.

The present invention may also be configured such that an angle of the long leg portion of the V-shaped element being inclined with respect to the axial direction is 50° to 80°, and an angle of the short leg portion of the V-shaped element being inclined is 5° to 30°.

Effects of the Invention

According to the present invention, it is possible to provide a flexible stent in which, when bending and placing the stent, a strut having a free end does not easily protrude outward and in which, when expanding the stent, shortening of the stent is suppressed.

BRIEF DESCRIPTION OF THE DRAWINGS

FIG. 15 is a schematic view illustrating shortening in a stent.

PREFERRED MODE FOR CARRYING OUT THE INVENTION

Figure 1:
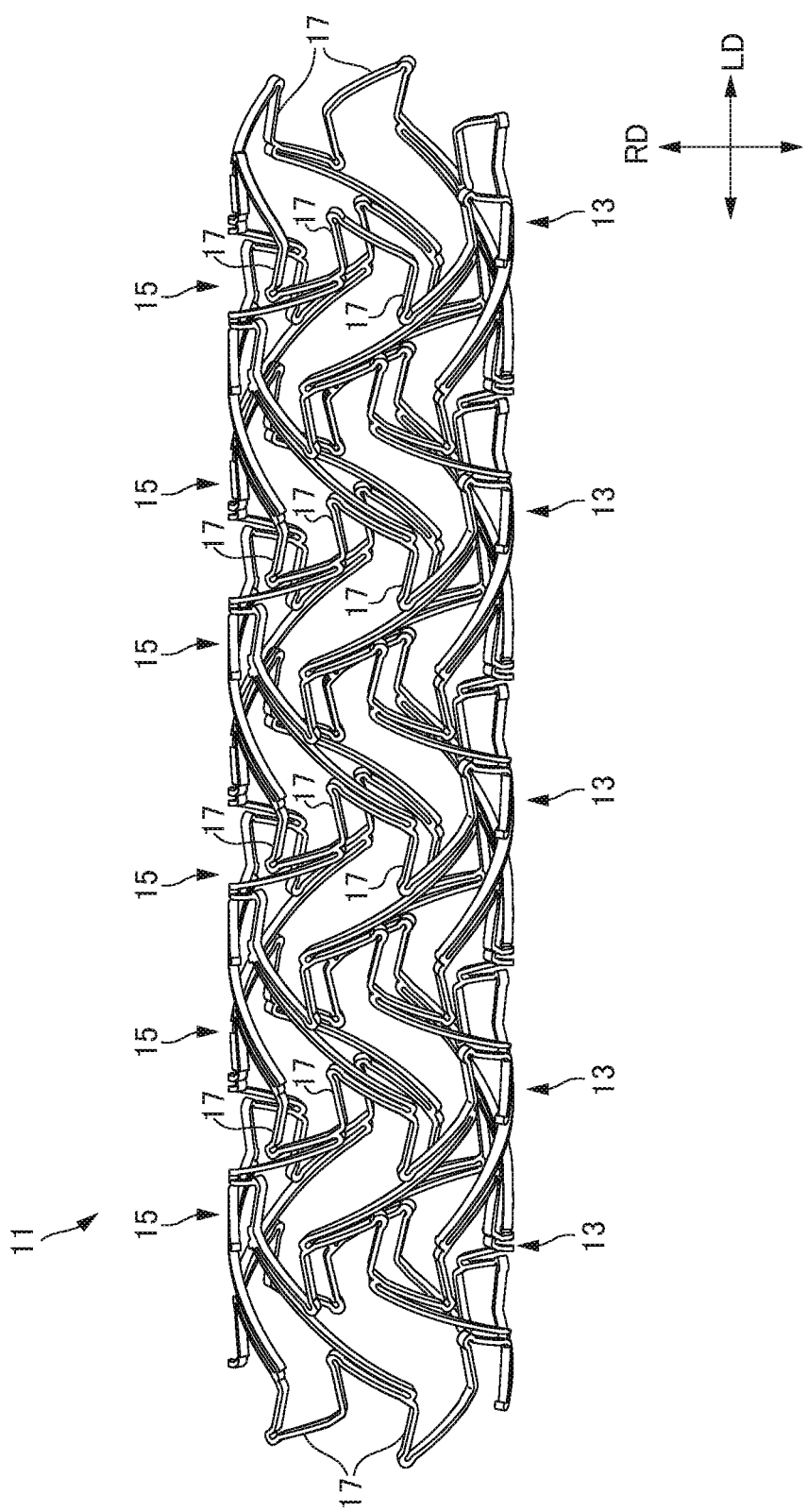
FIG. 1 is a perspective view of a flexible stent in a state of not being bent, according to an embodiment of the present invention.
Figure 2:
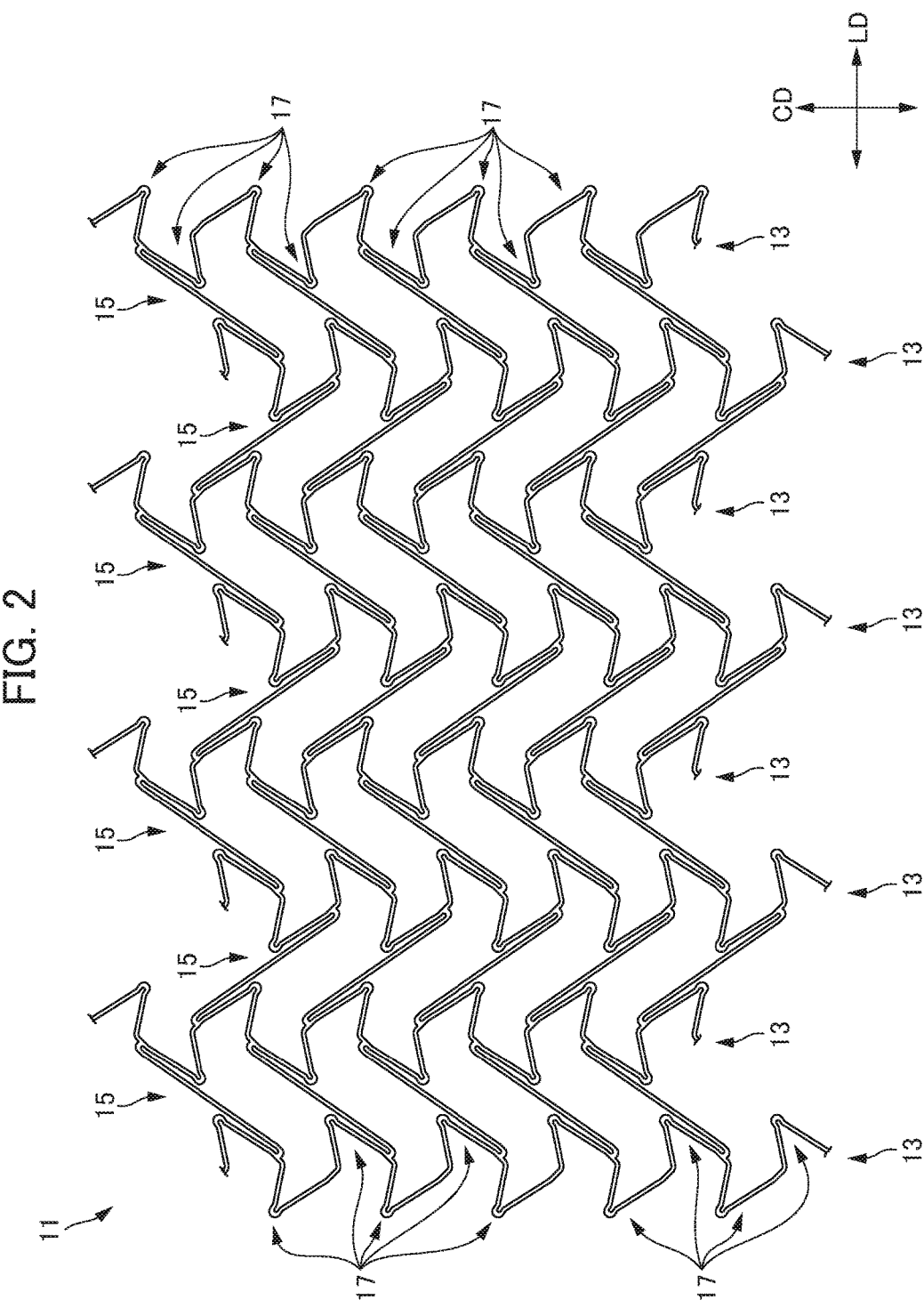
FIG. 2 is an expanded view illustrating the stent illustrated in FIG. 1 that is virtually expanded into a plane.
Figure 3:
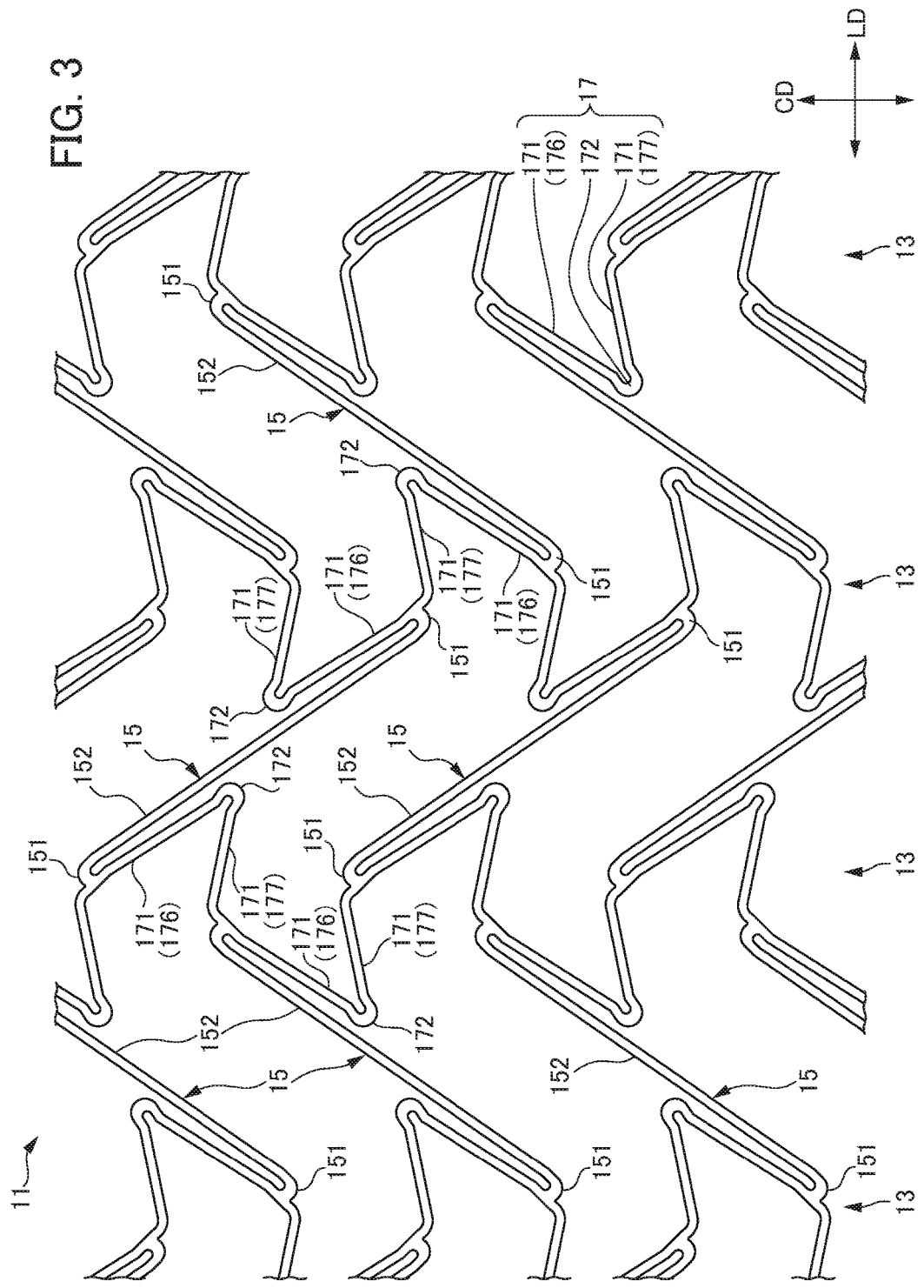
FIG. 3 is a partially enlarged view of the stent illustrated in FIG. 2.
Figure 4A:
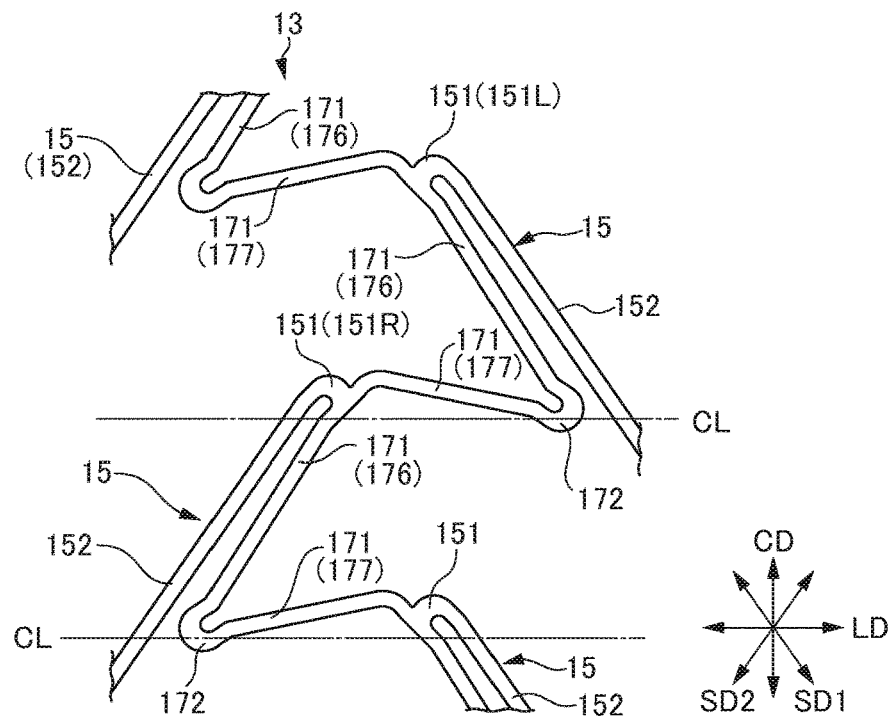
FIG. 4A is a partially enlarged view of the stent illustrated in FIG. 3.
Figure 4B:
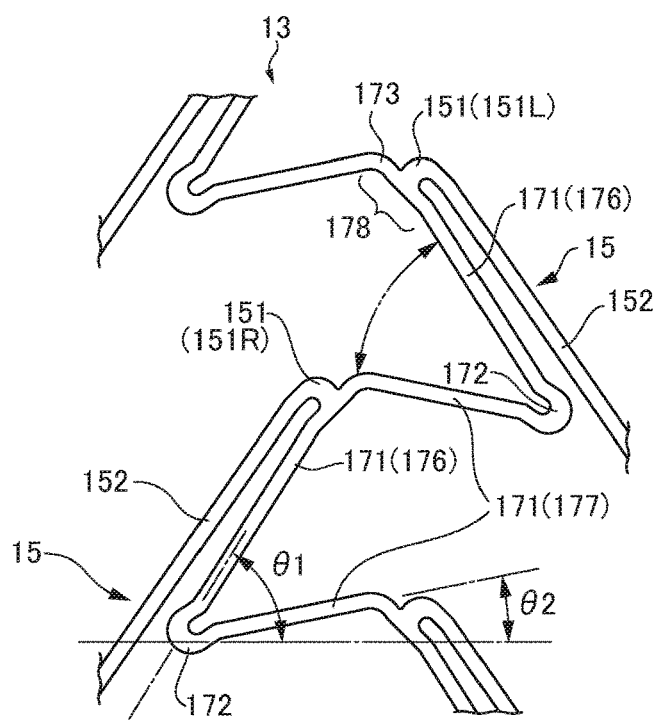
FIG. 4B is a partially enlarged view of the stent illustrated in FIG. 3.
Figure 5:
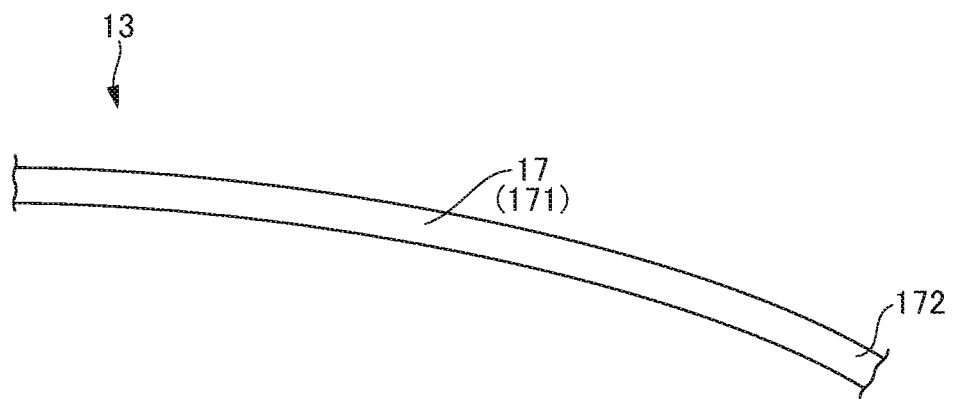
FIG. 5 is a side view of a V-shape element of a circular body of a stent.

In the following, an embodiment of a flexible stent according to the present invention will be described with reference to the drawings. With reference to FIGS. 1 to 5 first, the overall configuration of a flexible stent 11 according to the first embodiment of the present invention is described. FIG. 1 is a perspective view of a flexible stent in a state of not being bent, according to an embodiment of the present invention. FIG. 2 is an expanded view illustrating the stent illustrated in FIG. 1 that is virtually expanded into a plane. FIG. 3 is a partially enlarged view of the stent illustrated in FIG. 2. FIG. 4A is a partially enlarged view of the stent illustrated in FIG. 3. FIG. 4B is a partially enlarged view of the stent illustrated in FIG. 3. FIG. 5 is a side view of a V-shape element of a circular body of a stent.

As illustrated in FIGS. 1 and 2, the stent 11 is of a substantially cylindrical shape. A peripheral wall of the stent 11 has a structure of a mesh pattern in which a plurality of opened cells are spread in a circumferential direction. In FIG. 2, for the purpose of facilitating understanding of the structure of the stent 11, the stent 11 is illustrated in a state expanded in a plane. In the present specification, the peripheral wall of the stent 11 refers to a part that separates the inside from the outside of a cylinder with a substantially cylindrical shape of the stent 11. Furthermore, the term "cell" also refers to an opening or a compartment that is a part enclosed by the wire-shaped material forming the mesh pattern of the stent 11.

The stent 11 is formed of material having biocompatibility such as stainless steel, tantalum, platinum, gold, cobalt, titanium, or alloys of these. It is particularly preferable for the stent 11 to be formed of materials having a super elastic property such as a nickel titanium alloy.

As illustrated in FIGS. 1 to 3, the stent 11 includes a plurality of circular bodies 13 that are arranged in an axial direction (a longitudinal axial direction, a central axial direction) LD and a plurality of connection elements 15 that connect the circular bodies 13, 13 that are adjacent to each other in the axial direction LD.

As illustrated in FIGS. 3 to 4B, the circular body 13 includes a wavy-line pattern that is formed by connecting, in a circumferential direction, a plurality of V-shaped elements in substantially a V-shape. The V-shaped element 17 is formed by coupling two leg portions 171 with an apex 172. The wavy-line pattern is formed in a manner whereby a plurality of the V-shaped elements 17 are connected in a state in which the apices 172 are arranged to alternately face the opposite direction in the axial direction LD. When viewing in a radial direction RD perpendicular to the axial direction LD, a circular direction CD of the circular body 13 is not inclined with respect to (corresponds to) the radial direction RD. It should be noted that the circular direction CD of the circular body 13 may be inclined with respect to the radial direction RD.

Both ends 151 of each of the connection elements 15 connect two adjacent circular bodies 13, respectively, in the axial direction LD. The ends 151 of the connection elements 15 are connected with portions other than the apices 172 of the V-shaped elements 17 at the adjacent circular bodies 13 by extending in a direction different from the direction in which the leg portions 171 extend. The entire portion or a partial portion of the apex 172 of the V-shaped element 17 is a free end. In the present embodiment, every apex 172 is a free end. In other words, the stent 11 has a so-called open cell structure. The leg portion 171 including an unconnected apex 172 forms a strut having a free end.

The end 151 of the connection element 15 is connected to the leg portion 171 at each of the V-shaped elements 17 of which the apex 172 faces in the same direction in the axial direction LD. More specifically, when focusing attention on a plurality of connection elements 15 located between the two adjacent circular bodies 13, the plurality of connection elements 15 are connected to the leg portions 171 at each of the V-shaped elements 17 of which the apex 172 faces in the same direction in the axial direction LD. When viewing in another way, the plurality of connection elements 15 are connected to every other V-shaped element 17 in the circular direction CD. When viewing in the radial direction RD, the directions SD1 and SD2 (refer to FIG. 4A) in which intermediate portions 152 of the connection element 15 extend are inclined with respect to the axial direction LD.

The two leg portions 171, 171 of the V-shaped element 17 include a long leg portion 176 and a short leg portion 177. The adjacent V-shaped elements 17, 17 in the circular direction CD of the circular body 13 are connected so that the long leg portion 176 and the short leg portion 177 are adjacent each other. The end 151 of the connection element 15 is connected to the long leg portion 176 of the V-shaped element 17. One of the leg portions 171 (the long leg portion 176) extends along the intermediate portion 152 of the connection element 15. Both of the two leg portions 171 of the V-shaped element 17 (the long leg portion 176 and the short leg portion 177) are arranged on the same side with respect to the reference line CL which runs in parallel with the axial direction LD and passes through the apex 172. When viewing in the radial direction RD, the direction in which the leg portion 171 (the long leg portion 176 and the short leg portion 177) extends is inclined with respect to the axial direction LD.

When viewing in the radial direction RD, the intermediate portion 152 of the connection element 15 and the leg portion 171 of the V-shaped element 17 are linear. The long leg portion 176 extends along the intermediate portion 152 of the connection element 15. The leg portion 171 (the long leg portion 176) which extends along the intermediate portion 152 of this connection element 15 runs in parallel with the intermediate portion 152 of the connection element 15. The directions SD1 and SD2 (refer to FIG. 4A) in which the long leg portion 176 extends are inclined with respect to the axial direction LD. The direction in which one end 151L of the connection element 15 is bent and the direction in which the other end 151R of the connection element 15 is bent are opposite. The direction in which the end 151 of the connection element 15 extends and the direction in which the intermediate portion 152 of the connection element 15 extends are substantially perpendicular to each other. The matter of being substantially perpendicular herein means that the angle is 90°±5°.

As illustrated in FIG. 4B, the angle θ1 of the long leg portion 176 of the V-shaped element 17 being inclined with respect to the axial direction LD (the reference line CL) is 50° to 80°. The angle θ2 of the short leg portion 177 of the V-shaped element 17 being inclined is 5° to 30°.

The end 151 of the connection element 15 is connected in the proximity of a connection portion 173 of the adjacent V-shaped elements 17 and 17 in the circular direction of the circular body 13. The end 151 of the connection element 15 is connected to a portion 178 which is opposite to the apex 172 at the long leg portion 176 of the V-shaped element 17 and which is longer than the short leg portion 177. A curved arrow of the two-dashed line in FIG. 4B shows a location corresponding to the length of the short leg portion 177 at the long leg portion 176.

As illustrated in FIG. 5, the V-shaped element 17 is rounded in the thickness direction of the V-shaped element 17 along the shape of a virtual outer circumferential curved face of the flexible stent 11. The virtual outer circumferential curved face is substantially in a columnar shape. When viewing in the radial direction RD, the V-shaped element 17 is inclined with respect to the axial direction LD and extends toward the apex 172. Therefore, the V-shaped element 17 is rounded on a three dimensional curved face in the thickness direction of the V-shaped element 17. The V-shaped element 17 that is rounded on such a three dimensional curved face is easily obtained by laser-machining a substantially cylindrical tube.

It should be noted that, although the V-shaped element 17 is illustrated as being rounded two-dimensionally in FIG. 5, it is actually rounded on a three dimensional curved face. Furthermore, if a sheet-like material is formed in a substantially cylindrical shape after laser-machining to make it in a meshed shape, generally speaking, the V-shaped element 17 in such a case is not rounded on a three dimensional curved face in the thickness direction of the V-shaped element 17. Generally speaking, this is because the width of the leg portion 171 of the V-shaped element 17 is extremely narrow and the rigidity of the leg portion 171 of the V-shaped element 17 in the width direction is extremely high.

Figure 6:
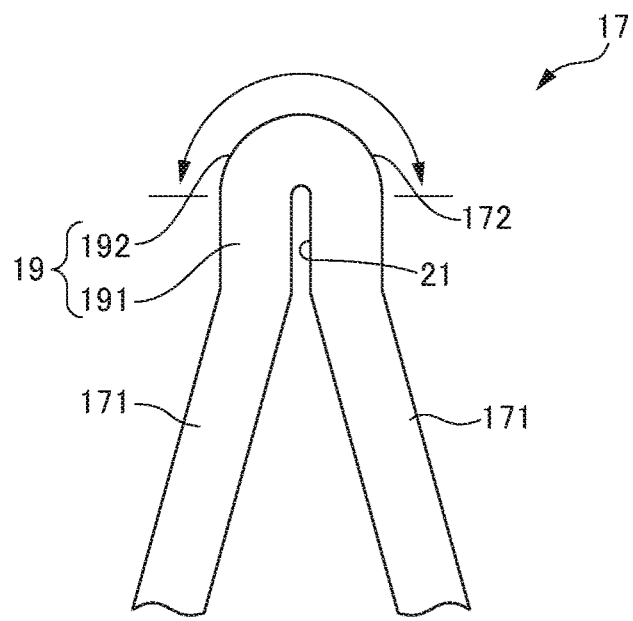
FIG. 6 is a partially enlarged view illustrating a first embodiment of an apex of the V-shaped element of the circular body of the stent.
Figure 7:
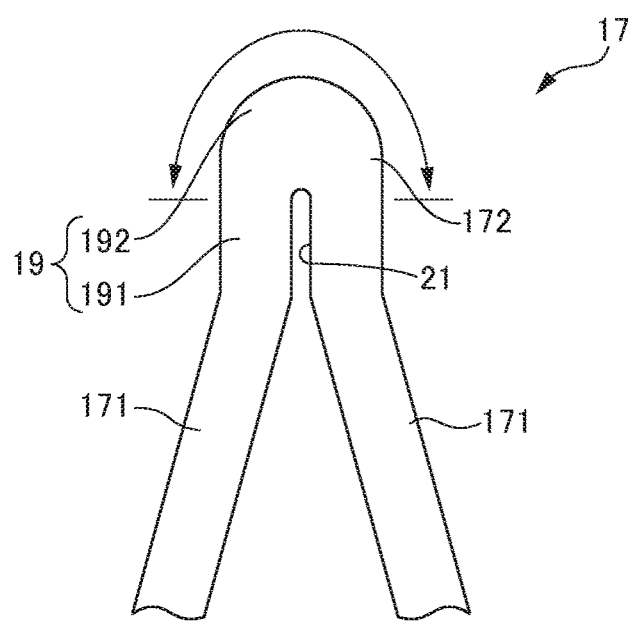
FIG. 7 is a partially enlarged view illustrating a second embodiment of an apex of the V-shaped element of the circular body of the stent.
Figure 8:
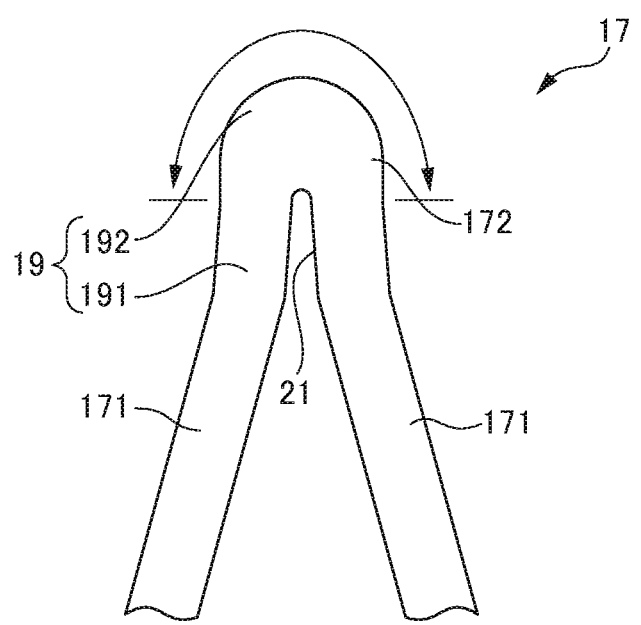
FIG. 8 is a partially enlarged view illustrating a third embodiment of an apex of the V-shaped element of the circular body of the stent.
Figure 9:
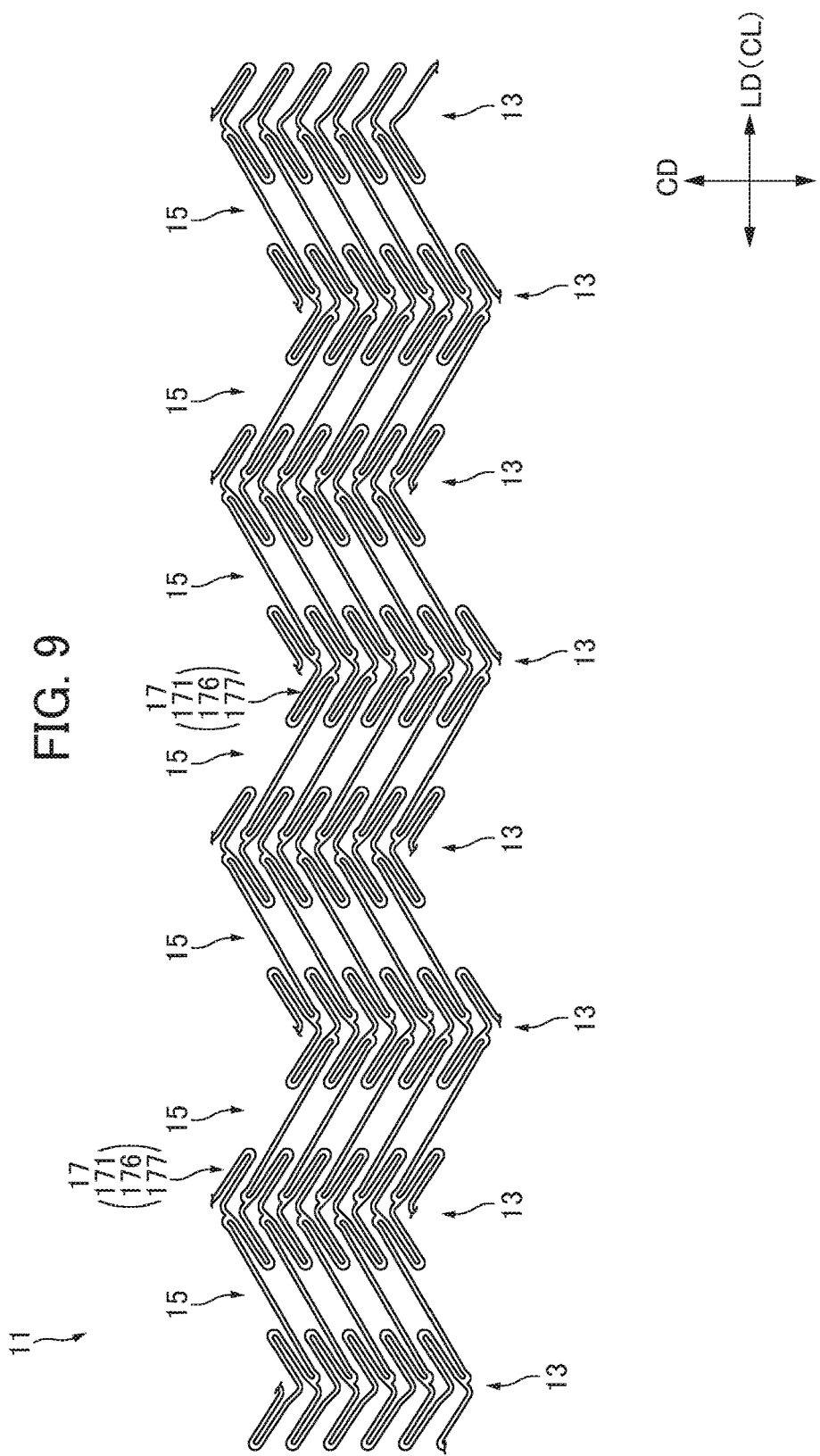
FIG. 9 is an expanded view of a stent virtually expanded into a plane, in a state in which a tube is laser-machined and not stretched.
Figure 10:
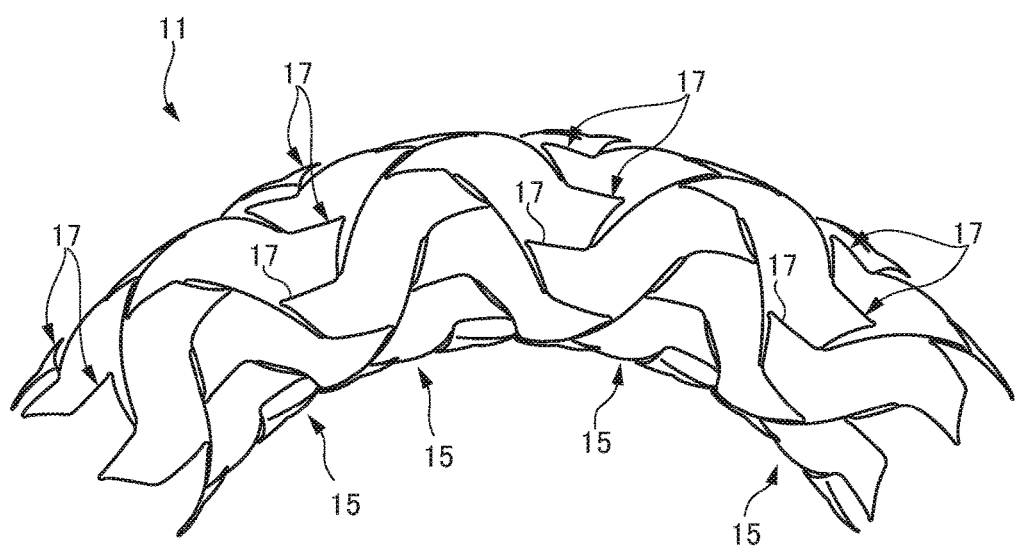
FIG. 10 is a perspective view illustrating a state in which the stent illustrated in FIG. 1 is bent.
Figure 11:
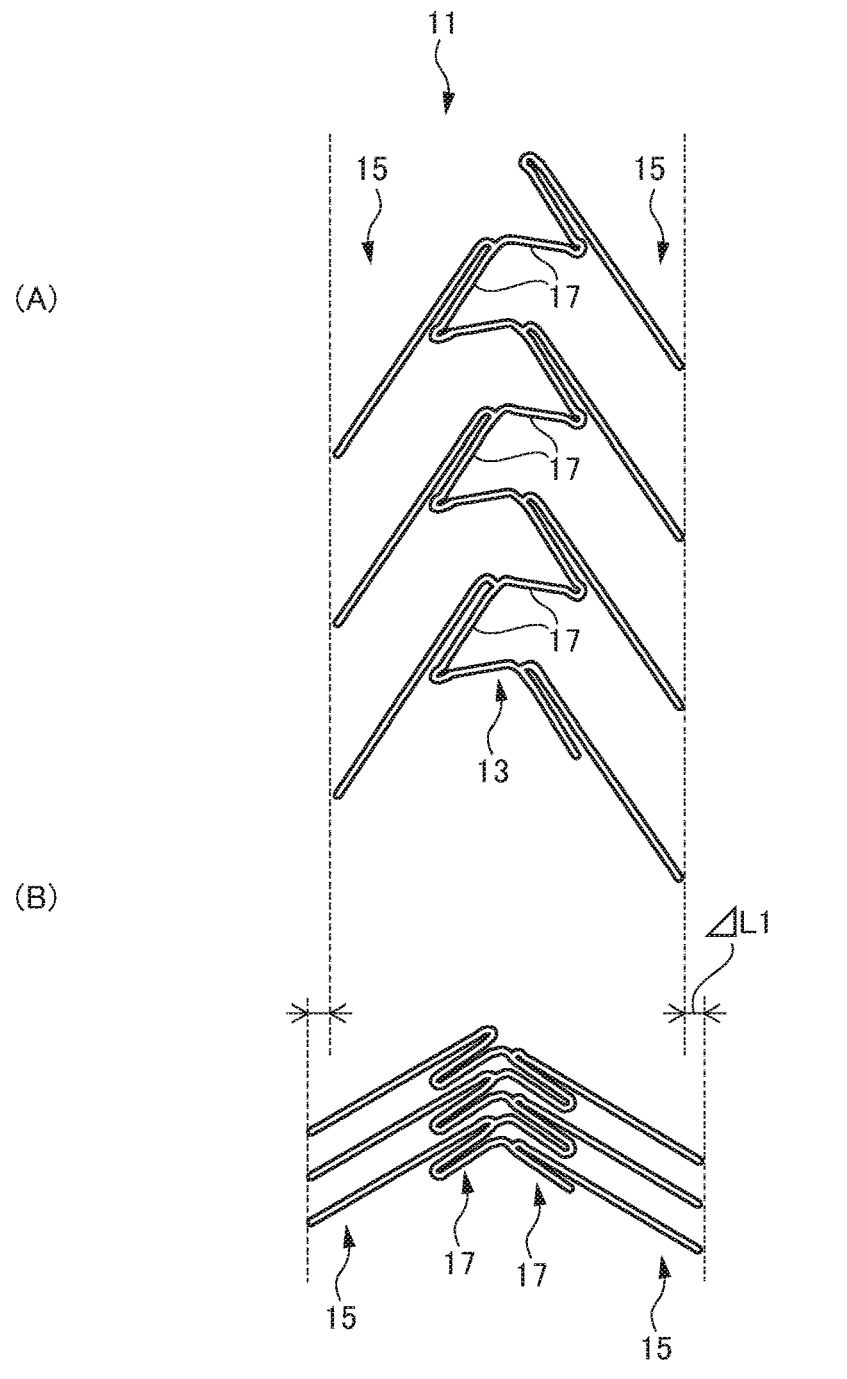
FIG. 11 is a view illustrating a difference in length of an axial direction of a stent according to the present embodiment between the time of being expanded and the time of being radially reduced in an expanded state.
Figure 11:
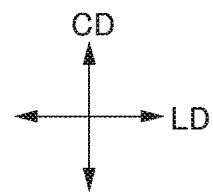
Figure 12:
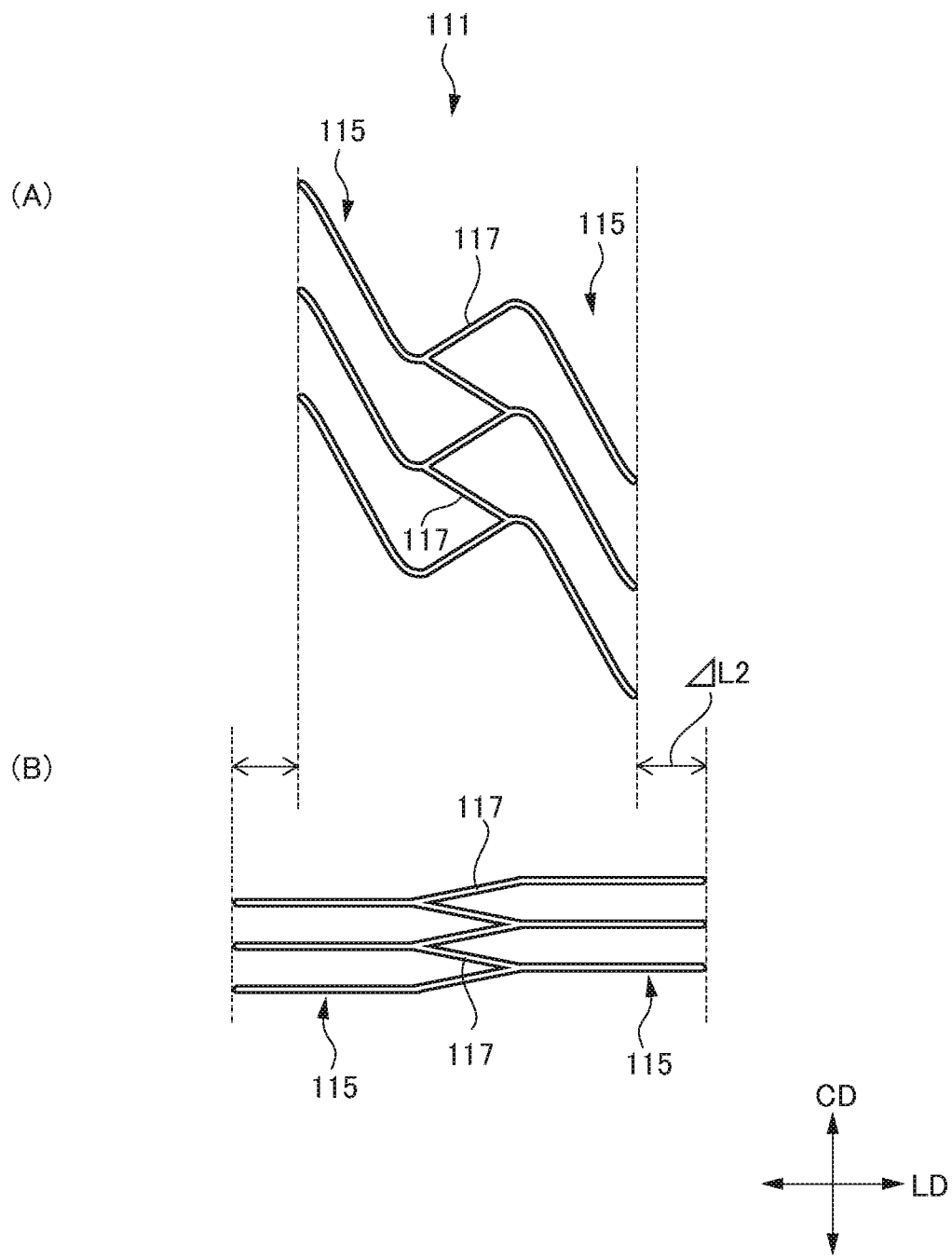
FIG. 12 is a view illustrating a difference in length of an axial direction of a stent according to a conventional example between the time of being expanded and the time of being radially reduced in an expanded state.
Figure 13:
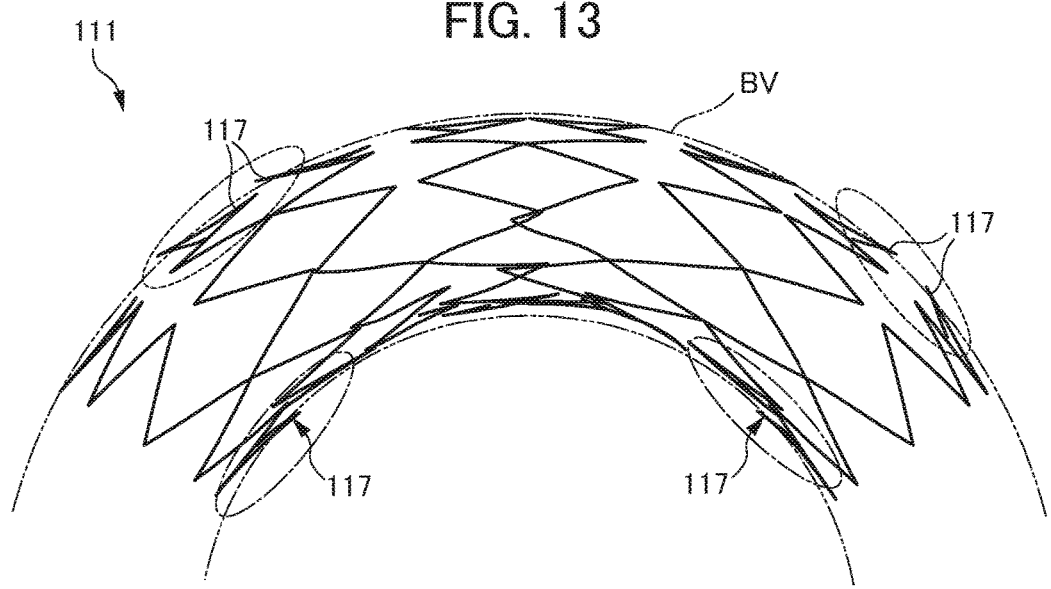
FIG. 13 is a schematic view illustrating a state of a strut in a state in which a conventional strut is bent.
Figure 14:
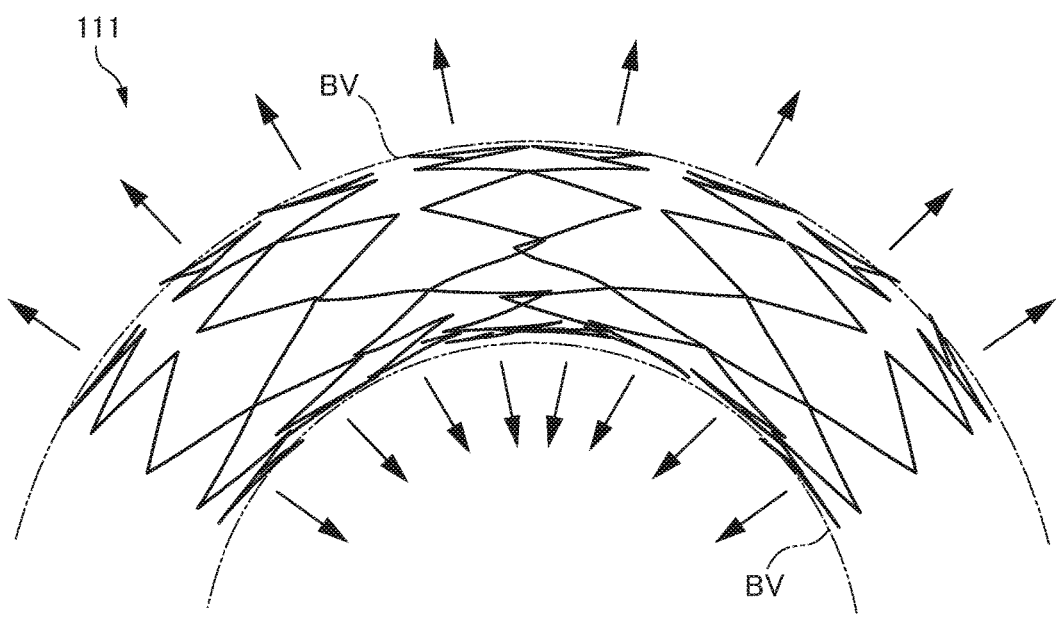
FIG. 14 is a schematic view illustrating a state of stress in a state in which a conventional stent is bent.

FIG. 6 is a partially enlarged view illustrating a first embodiment of an apex of the V-shaped element of the circular body of the stent. FIG. 7 is a partially enlarged view illustrating a second embodiment of an apex of the V-shaped element of the circular body of the stent. FIG. 8 is a partially enlarged view illustrating a third embodiment of an apex of the V-shaped element of the circular body of the stent. FIG. 9 is an expanded view of a stent virtually expanded into a plane, in a state in which a tube is laser-machined and not stretched. FIG. 10 is a perspective view illustrating a state in which the stent illustrated in FIG. 1 is bent. FIG. 11 is a view illustrating a difference in length of an axial direction of a stent according to the present embodiment between the time of being expanded and the time of being radially reduced in an expanded state. FIG. 12 is a view illustrating a difference in length of an axial direction of a stent according to a conventional example between the time of being expanded and the time of being radially reduced in an expanded state. FIG. 13 is a schematic view illustrating a state of a strut in a state in which a conventional strut is bent.

As illustrated in FIGS. 6 to 8, a knob portion 19 is formed at the apex 172 of the V-shaped element 17. The knob portion 19 includes an extension portion 191 which extends linearly and is inclined with respect to the axial direction LD and a substantially semicircle portion (tip portion) 192 formed at a tip thereof. The extension portion 191 has a width broader than the width of the connection element 15. Furthermore, at the apex 172 of the V-shaped element 17, a slit 21 is formed that extends from the inner peripheral portion along a direction in which the extension portion 191 extends. Therefore, two leg portions 171 are connected to a region of the extension portion 191 in which the slit 21 is not provided and the substantially semicircle portion 192 of the knob portion 19. It should be noted that, although it is preferable for the tip portion 192 to be substantially a semicircle portion, it may not be a substantially semicircle portion (not illustrated). The knob portion 19 exerts an effect of reducing metal fatigue. The slit 21 exerts an effect of improving the reduction of the radius of the stent 11.

The deformation of the V-shaped element 17 is performed around a valley-side portion of the base (inner peripheral portion) of the V-shaped element 17, and a portion which substantially contributes to deformation is a mountain side portion of the apex 172 of the V-shaped element 17 (a range shown by the two-way arrow at the upper portion of FIGS. 6 to 8), in particular, the outer peripheral portion thereof. Therefore, as illustrated in FIGS. 6 to 8, the stent 11 is configured so that the knob portion 19 which includes the extension portion 191 and the substantially semicircle portion 192 and has a width wider than the width of the connection element 15 is formed at the apex 172 so as to extend the apex 172.

More specifically, it is configured such that the extension portion 191 which extends in the axial direction LD is provided between the leg portion 171 of the V-shaped element 17 and the substantially semicircle portion 192, and the apex 172 is caused to be offset outward from the valley side portion (the inner peripheral portion) of the base of the V-shaped element 17 which becomes a deformation base. This configuration makes the outer peripheral portion of the apex 172 long. In order to prevent the adjacent knob portions 19 in the circumferential direction when radially reduced from becoming a factor of being in contact with each other which hinders the reduction of radius, as illustrated in FIGS. 6 to 8, it is preferable that the extension portion 191 is formed by a linear portion which extends in the axial direction LD.

In addition, in a case in which the slit 21 that extends from the inner peripheral portion of the apex 172 is formed at the apex 172 of the V-shaped element 17, the deformation of the V-shaped element 17 is performed around the tip of the slit 21 (the upper end of the slit 21 of FIGS. 6 to 8). The main portion that is involved with the deformation by crimping and expanding is a portion that is located outward more than the tip of the slit 21 in the V-shaped element 17. Therefore, the configuration in which the length of the extension portion 191 is longer than the length of the slit 21 and the extension portion 191 extends beyond the tip of the slit 21, as illustrated in FIG. 7, is more preferable than the configuration in which the length of the extension portion 191 is equivalent to or shorter than the length of the slit 21, as illustrated in FIG. 6.

As illustrated in FIGS. 6 and 7, the opposite side edges of the slit 21 are linear and extend substantially in parallel. In addition, as illustrated in FIG. 8, the opposite side edges of the slit 21 may not extend substantially in parallel (for example, these may become slightly wider toward the leg portions 171). Furthermore, the opposite side edges of the slit 21 may not be linear (not illustrated).

The stent 11 is inserted into a catheter in a state of being radially reduced, extruded by an extruder such as a pusher and moved in the catheter, and expanded at a site of pathology. At this moment, the force in the axial direction LD applied by the extruder interacts between the circular body 13 and the connection element 15 of the stent 11 to propagate over the entire stent 11.

The stent 11 having the abovementioned structure is produced by laser-machining a material having biocompatibility, and more preferably, is a tube made of a super elastic alloy. When producing a stent made of a super elastic alloy tube, in order to reduce production cost, an approximately 2 to 3 mm tube is laser-machined once. FIG. 9 illustrates the stent 11 at this moment, i.e., an expanded state of the stent 11 virtually expanded into a plane, in a state in which the tube is laser-machined and not stretched. In this state, both of the two leg portions 171 of the V-shaped element 17 (the long leg portion 176 and the short leg portion 177) run in parallel and, furthermore, arranged on the same side with respect to the axial direction LD (the reference line CL). Thereafter, this is expanded up to a desired radius. The stent 11 at this moment is in a state of being virtually expanded into a plane as illustrated in FIG. 2. It is preferable to produce the stent 11 by performing shape-memory treatment on the tube. In addition, the method of producing the stent 11 is not limited to laser-machining and includes other methods such as cutting processing.

Next, a method of using the stent 11 is described. A catheter is inserted into a blood vessel of a patient and the catheter is delivered to a site of pathology. Then, the stent is radially reduced (crimped) and placed in the catheter. Next, the stent in a state of being radially reduced is pushed out along a lumen of the catheter using an extruder such as a pusher and the stent 11 is extruded from a tip of the catheter and expanded at a site of pathology. Then, it is possible to place the stent 11.

According to the stent 11 of the present embodiment having the abovementioned configuration, the following effect is exerted, for example. The stent 11 of the present embodiment includes each of the abovementioned configurations. For example, the wavy-line pattern is formed in such a manner that the plurality of V-shaped elements 17 in a substantially V-shape made by coupling the two leg portions 171 at the apex 172 are connected in a state in which the apices 172 are arranged to alternately face opposite directions in the axial direction DL. When viewing in the radial direction RD, the direction in which the intermediate portion 152 of the connection element 15 extends is inclined with respect to the axial direction LD. One of the two leg portions 171 (the long leg portion 176) extends along the intermediate portion 152 of the connection element 15.

Furthermore, the end 151 of the connection element 15 is connected to the leg portion 171 at each of the V-shape elements 17 of which the apices 172 face in the same direction in the axial direction LD. The both of the two leg portions 171 of the V-shape element 17 are arranged on the same side with respect to the reference line CL. The V-shape element 17 is rounded in the thickness direction of the V-shape element 17 along the shape of a virtual outer circumferential curved face of the flexible stent 11. The intermediate portion 152 of the connection element 15 and the leg portion 171 of the V-shape element 17 are linear. The leg portion 171 that extends along the intermediate portion 152 of the connection element 15 runs in parallel with the intermediate portion 152 of the connection element 15. The two leg portions 171 of the V-shape element 17 consist of the long leg portion 176 and the short leg portion 177. The adjacent V-shape elements 17 in the circular direction CD of the circular body 13 are connected so that the long leg portion 176 is adjacent to the short leg portion 177. The end 151 of the connection element 15 is connected to the long leg portion 176 of the V-shape element 17. The end 151 of the connection element 15 is connected to the portion 178 which is opposite to the apex 172 at the long leg portion 176 of the V-shape element 17 and which is longer than the short leg portion 177.

With the synergistic effect from a part or all of each of the configurations, as illustrated in FIG. 10, even when bending and placing the stent 11 according to the present embodiment at a bent portion of a blood vessel, etc., the V-shape element 17 that forms a strut having a free end does not protrude radially outward from the stent 111 in a flared shape. As a result, the stent 11 according to the present embodiment does not damage the tissue of tubular organs in a living body such as a blood vessel easily, for example, the risk of causing thrombus on the inner side of the stent in the radial direction is low, the adhesion to the blood vessel wall in a tortuous blood vessel is superior, and thus stress concentration to the blood vessel wall is reduced.

With the synergistic effect from a part or all of each of the configurations, as illustrated in FIG. 11, when the stent 11 which is mounted to a catheter in a state of being radially reduced (refer to FIG. 11(B)) is expanded in a blood vessel during operation (refer to FIG. 11(A), the total length of the stent 11 is shortened in the axial direction LD more than when crimped (radially reduced). The shortened length of this case is shown as ΔL1.

As a comparison target, the stent 111 in the conventional example of FIG. 12 is shown. As illustrated in FIG. 12, when the stent 111 which is mounted to a catheter in a state of being radially reduced (refer to FIG. 12(B) is expanded in a blood vessel during operation (refer to FIG. 12(A), the total length of the stent 111 is shortened in the axial direction LD more than when crimped (radially reduced). The shortened length of this case is shown as ΔL2. It should be noted that the reference numeral 115 shows a connection element. As is clear from the comparison between ΔL1 shown in FIG. 11 and ΔL2 shown in FIG. 12, the stent 11 according to the present embodiment has a high effect of suppressing shortening.

Although the stent according to the present invention is described with reference to the embodiment, the present invention is not limited to the embodiment. For example, the V-shape element 17 may not be rounded in the thickness direction. The intermediate portion 152 of the connection element 15 and the leg portion 171 of the V-shape element 17 may not be linear. The leg portion 171 that extends along the intermediate portion 152 of the connection element 15 may not be in parallel with the intermediate portion 152 of the connection element 15. The lengths of the two leg portions 171 of the V-shape element 17 may be the same.

EXPLANATION OF REFERENCE NUMERALS 11 stent (flexible stent)
13 circular body
15 connection element
151 end
152 intermediate portion
17 V-shape element
171 leg portion
172 apex
173 connection portion
176 long leg portion
177 short leg portion
178 long portion
LD axial direction
RD radial direction
CD circular direction

The invention claimed is:
1. A flexible stent comprising:
a plurality of circular bodies each having a wavy-line pattern and arranged side-by-side in an axial direction of the stent; and
a plurality of connection elements that connect the circular bodies that are adjacent to each other and extend around an axis of the stent,
wherein the wavy-line pattern is formed in such a manner that a plurality of V-shaped elements each in a substantially V-shape made by coupling two leg portions at an apex of each V-shaped element are connected in a state in which apexes of the V-shaped elements are arranged to alternately face opposite directions in the axial direction,
wherein a direction in which a first end of each connection element is bent and a direction in which a second end of each connection element is bent are opposite,
wherein the first end of each connection element is connected with one of first two leg portions at a location other than an apex of a first V-shaped element of a first circular body and the second end of each connection element is connected with one of second two leg portions at a location other than an apex of a second V-shaped element of a second circular body which is adjacent to the first circular body by extending in a direction different from a direction in which the one of the first two leg portions and the one of the second two leg portions extend,
wherein, when viewing in a radial direction perpendicular to the axial direction, a direction in which an intermediate portion of each connection element extends is inclined with respect to the axial direction, wherein the one of the first two leg portions which is configured to connect to the first end of each connection element and the one of the second two leg portions which is configured to connect to the second end of each connection element extend along the intermediate portion of each connection element, and a direction in which the one of the first two leg portions extends and a direction in which the one of the second two leg portions extends are configured to be in a non-crossing relation with a direction in which the intermediate portion extends.

2. The flexible stent according to claim 1, wherein the apex of the first V-shaped element and the apex of the second V-shaped element face each other in a same direction in the axial direction.

3. The flexible stent according to claim 1, wherein both of the two leg portions of each V-shaped element are arranged on the same side with respect to a reference line which runs in parallel with the axial direction and passes through the apex of each V-shaped element.

4. The flexible stent according to claim 1, wherein each V-shaped element is rounded in a thickness direction of each V-shaped element along a shape of a substantially columnar outer circumferential curved face of the flexible stent in a rolled state.

5. The flexible stent according to claim 1, wherein a direction in which each of the first end and the second end of each connection element extends and a direction in which the intermediate portion of each connection element extends are substantially perpendicular to each other.

6. The flexible stent according to claim 1, wherein the intermediate portion of each connection element and the two leg portions of each V-shape element are linear, and one of the two leg portions that extends along the intermediate portion of each connection element runs in parallel with the intermediate portion of each connection element.

7. The flexible stent according to claim 1, wherein the first end of each connection element is connected in a proximity of a connection portion of the first V-shaped element and the second end of each connection element is connected in a proximity of a connection portion of the second V-shaped element.

8. The flexible stent according to claim 1, wherein the two leg portions of each V-shaped element consist of a long leg portion and a short leg portion which is shorter than the long leg portion, and one V-shaped element and an adjacent V-shaped element in a same circular body are connected around the axis of the stent, so that a long leg portion of the one V-shaped element is connected to a short leg portion of the adjacent V-shaped element.

9. The flexible stent according to claim 8, wherein each of the first end and the second end of each connection element is connected to the long leg portion of each V-shaped element.

10. The flexible stent according to claim 8, wherein each of the first end and the second end of each connection element is connected to a portion which is opposite to an apex at the long leg portion of each V-shape element and which is longer than the short leg portion.

11. The flexible stent according to claim 8, wherein an angle of the long leg portion of each V-shaped element being inclined with respect to the axial direction is 50° to 80°, and an angle of the short leg portion of each V-shaped element being inclined is 5° to 30°.

* * * * *